US008865809B2

(12) United States Patent
Townend et al.

(10) Patent No.: US 8,865,809 B2
(45) Date of Patent: Oct. 21, 2014

(54) SLIP AND ANTIBLOCKING AGENT

(75) Inventors: Jonathan David Townend, Hull (GB); John Latus, North Ferriby (GB); Philip John McCoy, Hull (GB); Adam John Maltby, Leven (GB); David Andrew Parker, Hessle (GB)

(73) Assignee: Croda International PLC, Goole, East Yorkshire (GB)

( * ) Notice: Subject to any disclaimer, the term of this patent is extended or adjusted under 35 U.S.C. 154(b) by 197 days.

(21) Appl. No.: 13/380,445

(22) PCT Filed: Jun. 18, 2010

(86) PCT No.: PCT/GB2010/001197
§ 371 (c)(1),
(2), (4) Date: Dec. 22, 2011

(87) PCT Pub. No.: WO2010/149952
PCT Pub. Date: Dec. 29, 2010

(65) Prior Publication Data
US 2012/0101201 A1    Apr. 26, 2012

(30) Foreign Application Priority Data
Jun. 23, 2009   (GB) .................................. 0910781.4

(51) Int. Cl.
*C08K 5/00*      (2006.01)
*C08K 5/20*      (2006.01)
*C07C 233/05*    (2006.01)
*C08L 23/10*     (2006.01)

(52) U.S. Cl.
CPC ............... *C07C 233/05* (2013.01); *C08L 23/10* (2013.01); *C08K 2201/014* (2013.01); *C08K 5/20* (2013.01)
USPC .......................................... 524/210; 524/232

(58) Field of Classification Search
USPC ........................................................ 524/210
See application file for complete search history.

(56) References Cited

U.S. PATENT DOCUMENTS

| | | | |
|---|---|---|---|
| 2,013,108 | A | 9/1935 | Reppe et al. |
| 2,770,609 | A | 11/1956 | Symonds |
| 6,497,965 | B1 | 12/2002 | Longmoore et al. |
| 6,846,863 | B2 * | 1/2005 | Plume et al. .................. 524/211 |
| 7,267,862 | B1 | 9/2007 | Burke et al. |
| 2005/0232956 | A1 | 10/2005 | Bist et al. |
| 2005/0283011 | A1 | 12/2005 | Hoong et al. |
| 2007/0020472 | A1 | 1/2007 | Mills et al. |

FOREIGN PATENT DOCUMENTS

| | | |
|---|---|---|
| EP | 0249342 | 12/1987 |
| EP | 0415697 | 3/1991 |
| EP | 0471571 | 2/1992 |
| JP | 48-13935 | 5/1973 |
| JP | 05-262676 | 10/1993 |
| JP | 11-010811 | 1/1999 |
| JP | 2001-508060 | 6/2001 |
| JP | 2003-523975 | 8/2003 |
| JP | 2004-002507 | 1/2004 |
| JP | 2005-500305 | 1/2005 |
| JP | 2006-096736 | 4/2006 |
| WO | WO 98/30532 | 7/1998 |
| WO | WO 98/46672 | 10/1998 |
| WO | WO 99/02485 | 1/1999 |
| WO | WO 01/59067 | 8/2001 |
| WO | WO 2003/000173 | 1/2003 |
| WO | WO 2003/031543 | 4/2003 |
| WO | WO 2005/085340 | 9/2005 |

OTHER PUBLICATIONS

Cason et al., J. Org. Chem., 15(1), 135-138, 1950.*
Biermann, Ursula et al. "Synthesis of alkyl-branched fatty acids," *Eur. J. Lipid Sci. Technol.*, vol. 110 (2008) 805-811.
Ngo, Helen L. et al. "Zeolite-catalyzed isomerization of oleic acid to branched-chain somers," *Eur. J. Lipid Sci. Technol.*, vol. 108 (2007) 214-224.
Swern, Daniel et al. "Application of Urea Complexes in the Purification of Fatty Acids, Esters and Alcohols—II. Oleic Acid and Methyl Oleate from Olive Oil," *Journal of the American Oil Chemists' Society*, Dec. 1952, pp. 614-615 (XP008101973).
Schneider, A. K. et al. "The Synthesis of Some Methylated Fatty Acids," 1941 (XP002623521).
Prout, Franklin et al. "Branched-Chain Fatty Acids—VIII. Synthesis of Two Acids Containing a 3-Pentyl Symmetrical End-Grouping," 1948 (XP002623519).
Cason, James et al. "Branched-Chain Fatty Acids—IX. Synthesis of Acids with Symmetrical End-Groups" 1948 (XP002623517).
Cason, James et al. "Branched-Chain Fatty Acids—X. Synthesis of Acids with Branching Methyl Groups Near the Carboxyl" 1948 (XP002623516).
Cason, James et al. "Branched-Chain Fatty Acids—XL. Location of Branching Methyl Groups Near Carboxyl by Rate Studies of Amide Hydrolysis" 1948 (XP002623518).
Cason, James et al. "Branched-Chain Fatty Acids—XII. Synthesis in the Methyloctadecanoic Acid Series" 1949 (XP002623515).
Cason, James et al. "Branched-Chain Fatty Acids—XIII. Preparation of Branched and Normal Acids for Use in the Study of Melting Points of Binary Mixtures" 1949 (XP002623514).
Cason, James et al. "Branched-Chain Fatty Acids—XIV. Location of Branching Methyl Groups by Study of the Melting Points of Binary Mixtures of Branched and Normal Acids or Amides" 1949 (XP002623520).
Office Action mailed Oct. 8, 2013 in corresponding Chinese Patent Application No. 201080028119.X.
Examination Report mailed Jun. 24, 2014 in corresponding Japanese Application No. 2012-516840 (English translation only).

* cited by examiner

*Primary Examiner* — Hui Chin
(74) *Attorney, Agent, or Firm* — Jones Day

(57) ABSTRACT

A novel, branched, saturated, primary fatty acid amide is disclosed. Application areas are as a slip and/or antiblocking agent or mold release agent. The branched, saturated, primary fatty acid has a formula R—CO—NH$_2$ where R is a saturated, branched hydrocarbon chain having 11 to 23 carbon atoms, wherein at least 60% by weight of the R—CO—NH$_2$ molecules have monoalkyl branches and less than 25% by weight of the R—CO—NH$_2$ molecules have polyalkyl branches.

21 Claims, No Drawings

SLIP AND ANTIBLOCKING AGENT

CROSS REFERENCE TO RELATED APPLICATION

This application is the National Phase application of International Application No. PCT/GB2010/001197, filed Jun. 18, 2010, which designates the United States and was published in English. This application, in its entirety, is incorporated herein by reference.

The present invention relates to a novel, branched, saturated, primary fatty acid amide and its use as a slip and/or antiblocking agent.

In the manufacture of polyolefin and related copolymer films it is common practice to include slip agents in the polymer formulation. The slip characteristic of a polyolefin film or layer is a measure of the ability to slide one layer over another and is commonly expressed in terms of the film's coefficient of friction. The slip agents migrate to the surface of the polymer film and decrease the coefficient of friction between the film and rollers over which it is passed, thus facilitating the processing of the film. Furthermore the slip agents decrease the coefficient of friction between layers of the film when it is wound into rolls thereby facilitating unwinding of the rolls for further processing. In the manufactured polyolefin film the presence of slip agents facilitates handling in for example automatic packaging machinery.

The blocking characteristic of a polyolefin film or layer may be defined as the tendency of the film or layer to stick to itself by the application of even slight compression. If a film has a high tendency to block then the ability to stick to itself can cause deformation and tearing of the film during manufacture. Blocking can be reduced by addition of finely divided organic fillers like silica but the addition of too high an amount of filler can be detrimental to the optical properties of the film.

Fatty acid amides are well recognised in the plastics industry as conventional slip and/or blocking agents for use in polyolefin and related copolymer formulations. They are generally derived from aliphatic saturated and/or unsaturated fatty acids containing between 16 and 22 carbon atoms. Examples of such fatty acid amides typically fall into the following categories:

Primary fatty acid amides of general structure R—CO—NH2, both saturated and unsaturated, where R is a straight chain. Examples of monounsaturated primary fatty acid amides include amides derived from straight chain unsaturated acids which are exemplified by erucamide and oleamide. Use of oleamide was first patented by DuPont, in 1956 in U.S. Pat. No. 2,770,609. These monounsaturated straight chained primary fatty acid amides are still generally preferred commercially as they typically provide a greater reduction in coefficient of friction in the polyolefin films with coefficients of friction less than 0.2 as compared to their saturated counterparts, with coefficients of friction greater than 0.5.

Examples of saturated primary fatty acid amides include amides derived from straight chain saturated acids which are exemplified by stearamide and behenamide. In fact stearamide may itself be preferentially used as an antiblocking agent in combination with for example a monounsaturated primary fatty acid amide as slip agent. U.S. Pat. No. 6,846,863 A discloses use of linear saturated fatty acids, specifically behenamide, as slip agents in polyethylene screw caps for bottles.

Secondary fatty acid amides of general structure R—CO—NHR', where both R and R' are typically straight chains. Examples include stearyl erucamide, oleyl palmitamide, erucyl erucamide and stearyl stearamide. These typically have coefficients of friction between 0.3 and 0.5. These amides are used to a lesser extent as slip agents in the packaging industry, typically for medium slip applications where control speed of migration is required. These amides are also used as mould release agents in the injection moulding industry.

There is a single JP patent application filed in 1968, JP48-13935, which discloses branched fatty acid amides for use as slip agents in polyester films. These amides have an iodine value of 3 to 10. There is no direct disclosure of the structure of these amides but reference to a previous US filing, U.S. Pat. No. 6,846,863 B2, suggests that they are secondary fatty acids amides of general structure R—CO—NHR', where both R and R' are typically branched chains. In particular R—CO— is derived from a C18 branched monocarboxylic acid. The C18 branched monocarboxylic acid is manufactured as a by product of the polymerisation of the naturally occurring unsaturated oleic acid to produce dimer/trimer acid. Heating the oleic acid in the presence of certain catalysts produces dimeric, trimeric and higher polymeric products, but instead of polymerising, a portion of the acid rearranges to give a branched, monomeric fatty acid which can be isolated by distillation and then hydrogenated. The saturated branched, monomeric fatty acid is a mixture of various linear and mainly branched, both mono and poly branched, saturated acids which is known as C18 branched monocarboxylic acid or more commonly isostearic acid.

Commercial isostearic acid, manufactured as disclosed in this JP application, is typically a mixture of monocarboxylic acids having from 14 to 22 carbon atoms with about two thirds of these monocarboxylic acids having 18 carbon atoms. The 18 carbon atom acids include short, mainly methyl but also some ethyl, side chains, branching from the main chain mainly in the middle of the chain, typically about the carbon 9 position, e.g. from about the carbon 6 to about the carbon 12 position. Gas chromatographic analysis of a typical commercial isostearic acid sample (Prisorine 3505 available ex Croda Europe Ltd) indicates the presence of about 40% of monobranched, saturated fatty acid with 18 carbon atoms, and about 31% of polybranched, saturated fatty acid with 18 carbon atoms. Nuclear Magnetic Resonance (NMR) analysis of this sample indicates that 74% of the branching is methyl branching, 12.2% of the branching is ethyl branching and 9% of the branching is propyl branching.

Saturated bis amides such as ethylene bis stearamide, typically used as a release agent in polyvinylchloride (PVC) and acrylonitrile butadiene styrene (ABS) and ethylene bis oleamide, which is used as slip agent in high vinyl acetate content ethylene vinyl acetate (EVA) copolymers.

Whilst undoubtedly one of the main reasons for choice of slip agent is based on its ability to reduce coefficient of friction in the polymer there are several other factors which also influence the choice of slip agent for a specific polymer type. These include speed to reduce coefficient of friction and stability of the effect of the reduction of coefficient of friction, odour, taste and colour of the polymer and thermal and oxidative stability of the slip agent in the polymer.

Unsaturated primary fatty acid amides, whilst providing the greatest reduction in coefficient of friction, are more unstable to oxidation due to the presence of the double bond. They may also contain small amounts of polyunsaturates which will exacerbate the oxidative instability. Undesirable effects of such oxidation are known to include increased colour and odour of the polymers and also loss of slip properties and increased blocking.

The present invention is based on our discovery that certain novel, saturated, branched, primary fatty acid amides have coefficients of friction in polymers similar to those derived from their unsaturated fatty acid counterparts but with enhanced oxidative stability.

Accordingly the present invention provides a branched, primary fatty acid amide of formula I:

where R is a saturated, branched hydrocarbon chain having 11 to 23 carbon atoms, wherein at least 60% by weight of the R—CO—NH$_2$ molecules have monoalkyl branches and less than 25% by weight of the R—CO—NH$_2$ molecules have polyalkyl branches.

R is preferably a saturated, branched hydrocarbon chain having 13 to 23, more preferably 15 to 21, especially 17 to 21 carbon atoms.

Preferably at least 70%, more preferably at least 75%, especially at least 80% by weight of the R—CO—NH$_2$ molecules have monoalkyl branched. Preferably less than 20%, more preferably less than 15% and especially less than 10% by weight of the R—CO—NH$_2$ molecules have polyalkyl branches. The mono alkyl group is preferably positioned in the hydrocarbon chain away from the amide grouping, more preferably it is positioned in the middle of the hydrocarbon chain.

The monoalkyl branching may be methyl, ethyl, propyl or a mixture of. Preferably the monoalkyl branching is at least 80% methyl, more preferably at least 90% and especially at least 95% methyl.

The branched primary fatty acid amide of formula I can be derived from amidation of the corresponding branched monocarboxylic fatty acid, RCOOH, the corresponding branched acid chloride, RCOCl, or the corresponding branched fatty acid ester, RCOOR' where in each case R is as defined in formula I. R' is typically a saturated hydrocarbon chain and may be the same or different to R. R' may be straight chained or branched. Preferably the branched primary fatty acid amide of formula I is derived from amidation of the corresponding branched monocarboxylic fatty acid, RCOOH with ammonia, in the presence of a suitable catalyst. Examples of suitable catalysts include butyl isopropyl titanate. The crude amide produced by this process is purified by, for example, thin film distillation, recrystallisation, for example heptane recrystallisation or solvent washing, for example hexane washing.

Preferably the branched fatty acid amide of formula I is fully saturated. Examples of suitable branched primary fatty acid amide include isostearamide derived from the reaction of isostearic acid, wherein at least 60% by weight of the isostearic acid molecules have monoalkyl branches and less than 25% by weight of the isostearic acid molecules have polyalkyl branches, with ammonia, isobehenamide derived from the reaction of isobehenic acid, wherein at least 60% by weight of the isobehenic acid molecules have monoalkyl branches and less than 25% by weight of the isobehenic acid molecules have polyalkyl branches, with ammonia An especially preferred branched primary fatty acid amide of formula 1 is derived from the reaction of isostearic acid, wherein at least 60% by weight of the isostearic acid molecules have monoalkyl branches and less than 25% by weight of the isostearic acid molecules have polyalkyl branches, with ammonia.

For the corresponding branched monocarboxylic acid the preferably at least 70%, more preferably at least 75%, especially at least 80% by weight of the monocarboxylic acid molecules have monoalkyl branches. Preferably less than 20%, more preferably less than 15% and especially less than 10% of the monocarboxylic acid molecules have polyalkyl branches. The mono alkyl group is preferably positioned in the middle of the hydrocarbon chain. For the branched monocarboxylic acid, RCOOH, R preferably has 13 to 23, more preferably 15 to 21, especially 17 to 21 carbon atoms.

The saturated branched fatty acid, RCOOH, may be obtained by refining standard, commercial, corresponding saturated branched fatty acids, R$^2$COOH, where R$^2$ has 11 to 23 carbon atoms and typically 40% by weight of the R$^2$COOH molecules have mono alkyl branches and 31% by weight of the R$^2$COOH has poly alkyl branches (based on GC analyses). The commercial saturated, branched fatty acids, R$^2$COOH, are preferably manufactured as a by product of the polymerisation of the naturally occurring corresponding unsaturated fatty acid, R$^3$COOH to produce dimer/trimer acid. Heating the naturally occurring unsaturated fatty acid, where R$^3$ has 11 to 23 carbon atoms, in the presence of certain catalysts produces dimeric, trimeric and higher polymeric products. Instead of polymerising, a portion of the naturally occurring unsaturated fatty acid rearranges to give a branched, monomeric fatty acid which can be isolated by distillation and then hydrogenated. The saturated branched, monomeric fatty acid product, R$^2$COOH is a mixture of various linear and mainly branched, both mono and poly branched, saturated acids.

A further possible route to R$^2$COOH from R$^3$COOH is using a zeolite catalyst, for example, Ferrierite, of small pore diameter which restricts formation of the dimeric, trimeric and higher polymeric products in favour of the rearrangement reaction leading to the branched monomeric fatty acid which can be isolated by distillation and then hydrogenated.

Other routes to saturated branched fatty acids, R$^2$COOH, include hydroformylation of the corresponding alkene followed by oxidation of the resulting aldehyde. Also, specifically for when R$^2$ is an hydrocarbon chain of 17 carbon atoms, one commercial route is dimerisation of the corresponding C9 alcohol to isostearyl alcohol which is then oxidised to the corresponding isostearic acid.

The commercially obtained R$^2$COOH can be refined in a variety of ways, for example clathration, distillation, fractional crystallisation and chromatography. One preferred method of refining is a clathration process with urea and a lower alcohol. This clathration refining process may be carried out in the following way. Commercial non-refined saturated, branched fatty acid having 12 to 24 carbon atoms is dissolved in a mixture of urea and a lower alcohol and refluxed at 65-90, especially 68-70° C. for 1 to 2 hours. The lower alcohol preferably has 1 to 4 carbon atoms and especially preferred examples are methanol and ethanol because of the ease of their subsequent removal from the reaction mixture. The weight ratio of commercial non-refined saturated, branched fatty acid having 12 to 24 carbon atoms to urea may be from 7:1 to 1:7, preferably 5:1 to 1:5 and more preferably 5:1 to 1:1. The weight ratio of urea to lower alcohol may be from 1:1 to 1:25, preferably from 1:3 to 1:15 and especially from 1:4 to 1:10. The clear solution formed during reflux is allowed to cool and refrigerated until crystals of a urea clathrate are formed. The urea clathrate is separated either by filtering or centrifugation and the filtrate can be isolated, provided at least 60% by weight of the acid molecules have monoalkyl branches and less than 25% by weight of the acid molecules have polyalkyl branches. However it may be further mixed with urea and the lower alcohol and refluxed at 65-90, especially 68-70° C. for a further 1 to 2 hours in a second clathration process. The weight ratio of urea to lower alcohol for this second clathration process may be from 3:1 to 1:8, preferably from 2:1 to 1:5 and especially from 2:1 to 1:2. The clear solution formed during reflux is allowed to cool and refrigerated until crystals of a second urea clathrate are formed. This second urea clathrate is separated off and may be placed in a brine solution and heated in an oven until all of the second urea clathrate has dissolved. The refined saturated, branched fatty acid having 12 to 24 carbon atoms, wherein at least 60% by weight of the acid molecules have monoalkyl branches and less than 25% by weight of the acid molecules have polyalkyl branches, separates from the brine solution and can be isolated. Alternatively the second filtrate may be mixed with urea and the clathration process undertaken for a third time before the refined saturated, branched fatty acid having 12 to 24 carbon atoms, wherein at least 60% by weight of the acid molecules have monoalkyl branches and less than 25% by weight of the acid molecules have polyalkyl branches is obtained.

The clathration process may also be undertaken where urea is replaced by thiourea. The clathration process may also be undertaken where some of the lower alcohol is removed, typically by distillation, during the refluxing stage.

Preferably the refined saturated, branched fatty acid, RCOOH has R having 13 to 23 carbon atoms, more preferably 15 to 21 carbon atoms, especially 17 to 21 carbon atoms. Examples include refined isostearic acid and refined isobehenic acid.

Therefore in a further aspect of the invention a process for preparation of a branched primary fatty amide of formula I:

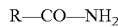

R—CO—NH$_2$ where R is a saturated, branched hydrocarbon chain having 11 to 23 carbon atoms wherein at least 60% by weight of the R—CO—NH$_2$ molecules have monoalkyl branches and less than 25% by weight of the R—CO—NH$_2$ molecules have polyalkyl branches which comprises
   a) refining a saturated branched fatty acid of formula R$^2$COOH where R2 has 11 to 23 carbon atoms to form RCOOH; followed by
   b) amidating the RCOOH with ammonia in the presence of a catalyst; then
   c) purifying the resultant branched primary fatty amide of formula I.

The branched, primary fatty acid amide of formula I preferably has an iodine value of not more than 2.8, more preferably not more than 2.5, even more preferably not more than 2.1 and especially not more than 1.8 g Iodine per 100 g.

The branched, primary fatty acid amide of formula I has been found to be of use as a slip and/or blocking agent in a polymer.

Therefore in a further aspect the present invention provides use of a branched, primary, fatty acid amide of formula I:

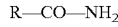

R—CO—NH$_2$ where R is a saturated, branched hydrocarbon chain having 11 to 23 carbon atoms, wherein at least 60% by weight of the R—CO—NH$_2$ molecules have monoalkyl branches and less than 25% by weight of the R—CO—NH$_2$ molecules have polyalkyl branches as a slip and/or blocking agent in a polymer.

In a further aspect the present invention provides use of a branched, primary, fatty acid amide of formula I:

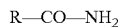

R—CO—NH$_2$ where R is a saturated, branched hydrocarbon chain having 11 to 23 carbon atoms, wherein the at least 60% by weight of the R—CO—NH$_2$ molecules have monoalkyl branches and less than 25% by weight of the R—CO—NH$_2$ molecules have polyalkyl branches as a mould release agent in a polymer.

Suitable polymers include olefin polymer compositions, both homopolymer and copolymers, for manufacture of films and shaped articles. Olefin polymer compositions include ethylene homopolymers and copolymers of ethylene with one or more co monomers. Examples of suitable co monomers include vinyl acetate, vinyl alcohol, methyl acrylate, ethyl acrylate and methacrylic acid and mixtures thereof which can be present at levels from 0 to 50% by weight with the ethylene. The polyethylene of the invention typically has a density from 0.875 to 0.96 g cm$^{-3}$. It is also typically characterised as having a melt index of 0.1 g/10 min to 30 g/10 min, measured at 190° C., under a load of 2.16 kg in accordance with ASTM D1238. Suitable olefin polymer compositions also include propylene homopolymers and copolymers of propylene with one or more co monomers. Suitable co monomers include ethylene, but-1-ene and hex-1-ene and mixtures thereof which can be present at levels from 0 to 30% by weight for both random and block copolymers. These copolymers can be present at levels greater than 30% by weight for use in thermoplastic olefins. The polypropylene of the invention typically has a density from 0.85 to 0.95 g cm$^{-3}$. It is also typically characterised as having a melt index of 0.1 g/10 min to 30 g/10 min, measured at 230° C., under a load of 2.16 kg. Films include both blown and cast films and monolayer and coextruded films. Shaped articles include those produced by conventional methods for producing shaped articles, for example extrusion, extrusion blow-moulding, extrusion thermoforming and injection moulding. Examples of shaped articles include closures, for example screw caps for bottles, bottles, containers, pails/buckets, garden furniture, car interior and under hood components, electrical components, fuel tanks and storage tanks.

Suitable polymers also include polystyrene. Suitable types of polystyrene and polystyrene with co monomers include high impact polystyrene (HIPS), general purpose polystyrene polymer (GPPS), ABS and styrene acrylonitrile (SAN) for manufacture of moulded articles. Examples of moulded articles include food containers and trays, furniture and housewares, CD cases, cosmetic containers. The branched primary fatty acid amide of the invention can act as both a slip agent and also aid mould release during polystyrene processing for such polystyrene articles.

Other suitable polymers include PVC. Examples of articles include plasticised and unplasticised films, sheet, moulded articles and sealant gaskets.

Preferred polymers are olefin polymer compositions. Even more preferred polymers are homopolymers and copolymers of polyethylene and polypropylene.

The branched primary fatty acid amide of the invention can be added directly to the polymer at the processing stage, pre-compounded or included via masterbatch. When added directly to the polymer for use in polyethylene based film the percentage of the branched primary fatty acid amide of the invention is preferably between 200 to 1500 ppm, more preferably 400 to 1000 ppm and especially 500 to 800 ppm. When added directly to the polymer for use in polypropylene based film, with or without co monomers, the percentage of the branched primary fatty acid amide of the invention is preferably between 500 to 3500 ppm, more preferably 1000 to 3000 ppm and especially 1200 to 1800 ppm. When added directly to the polymer for use in polyethylene based and polypropylene based moulded articles the percentage of the branched primary fatty acid amide of the invention is preferably between 0.1 to 3% by weight, more preferably 0.2 to 1.5% by weight and especially 0.2 to 0.9% by weight.

Use of the branched primary fatty acid amide of the invention as a slip and/or blocking agent leads to a coefficient of friction of preferably less than 0.50, more preferably less than 0.40 and especially less than 0.30.

When the branched primary fatty acid amide of the invention is used as a mould release agent the mould release force reduction is preferably at least 10%, more preferably at least 30% and especially at least 50% in a polymer as compared to a polymer without the mould release agent present.

Other known additives may be present in the polymer if required, for example known slip agents, a further blocking agent, antistatic agents, antioxidants, acid scavengers, colours/pigments, fillers/reinforcements, UV absorbers, light stabilisers, antifogging agents, nucleating agents, non migrating slip additives for example solid silicones or crosslinked polymethylmethacrylates (PMMA).

Examples of known slip agents include both saturated and unsaturated acid amides. A specific example is erucamide. These slip agents are typically present at levels of between 0.1 to 3% by weight in the polymer.

Examples of further blocking agents include natural and synthetic silica, calcium carbonate. These blocking agents are typically present at levels of between 500 to 5000 ppm in the polymer.

Examples of antistatic agents include glycerol esters, ethoxylated amines, alkanamides and sodium alkyl sulphonates. These agents are typically present at levels of between 0.05 to 3% in the polymer.

In a further aspect the present invention provides a process for increasing slip and reducing block of polyolefin films, both monolayer and coextruded, which process comprises fabricating said films and sheets from a polymer composition including a branched, primary, fatty acid amide of formula I:

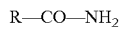
R—CO—NH$_2$ where R is a saturated, branched hydrocarbon chain having 11 to 23 carbon atoms, wherein at least 60% by weight of the R—CO—NH$_2$ molecules have monoalkyl branches and less than 25% by weight of the R—CO—NH$_2$ molecules have polyalkyl branches.

In a further aspect the present invention provides a polymer composition comprising
(A) 50 to 99.98% by weight of a polyolefin polymer
(B) 0.02 to 3% by weight of a branched, primary, fatty acid amide of formula I:

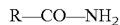
R—CO—NH$_2$ where R is a saturated, branched hydrocarbon chain having 11 to 23 carbon atoms, wherein at least 60% by weight of the R—CO—NH$_2$ molecules have monoalkyl branches and less than 25% by weight of the R—CO—NH$_2$ molecules have polyalkyl branches In a further aspect the present invention provides a polymer composition comprising
(A) 50 to 99.9% by weight of a polystyrene polymer
(B) 0.1 to 3% by weight of a branched, primary, fatty acid amide of formula I:

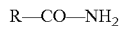
R—CO—NH$_2$ where R is a saturated, branched hydrocarbon chain having 11 to 23 carbon atoms, wherein at least 60% by weight of the amide molecules have monoalkyl branches and less than 25% by weight of the amide molecules have polyalkyl branches The following examples illustrate the invention. All parts and percentages are by weight unless otherwise stated.

EXAMPLE 1

Preparation of isostearic acid, wherein at least 60% by weight of the acid molecules have monoalkyl branches and less than 25% by weight of the acid molecules have polyalkyl branches by a two stage clathration process.

Commercial Isostearic acid (500 g, Prisorine 3505 ex Croda Europe Ltd) and Urea prills (500 g) were refluxed in methanol (2500 ml) for 2 hours. The solution was allowed to cool and then placed in a fridge (~4° C.) over night (~18 hours). Urea crystals that formed were filtered off and placed in a conical flask with brine solution. This was placed in an oven (60° C.) and stirred occasionally until all of the urea had dissolved. The resulting fatty material was pipette off the top of the brine and labelled U1.

Urea prills (500 g) were added to the filtrate and refluxed again for 2 hours before been allowed to cool and left in the fringe overnight. The urea crystals that formed were again filtered off and the urea was dissolved as before. The resulting fatty material was labelled U2.

The methanol was removed from the filtrate and the resulting sully was washed with warm brine solution to remove the remaining urea. The resulting fatty material was labelled Filtrate. All three fractions were dried using either sodium or magnesium sulphate.

Table 1 below illustrates the rough weights and yields for each of the fractions.

TABLE 1

| Fraction | Weight in g | % Yield |
|---|---|---|
| U1 | 120 | 24 |
| U2 | 88 | 18 |
| Filtrate | 272 | 54 |
| Losses | 20 | 4 |

Table 2 below shows the percentage of each of the main components of standard commercial isostearic acid in each fraction as determined by gas chromatographic (GC) analysis.

TABLE 2

| | Approximate GC Areas (%) | | |
|---|---|---|---|
| Fraction | Palmitic | Mono Alkyl Branched | Poly Alkyl Branched |
| U1 | 24 | 51 | 2 |
| U2 | 1 | 86 | 4 |
| Filtrate | 2 | 5 | 65+ |
| Commercial Isostearic Acid (Comparative) | 7 | 40 | 31 |

With the percentage for poly alkyl branched material it is unclear exactly how much is the poly alkyl branched material and how much of it is other species. The quoted percentage is for material that is definitely poly alkyl branched material.

U2 is the refined branched saturated monocarboxylic acid of the invention wherein at least 60% by weight of the acid molecules have monoalkyl branches and less than 25% by weight of the acid molecules have polyalkyl branches.

EXAMPLE 2

Preparation of isostearamide where at least 60% by weight of the amide molecules have monoalkyl branches and less than 25% by weight of the amide molecules have polyalkyl branches 88.0 g of U2 from Example 1 was placed in a miniclave, under a slight nitrogen pressure and heated to 170° C. with stirring. The nitrogen was vented off and excess of 300 psi ammonia was added. Periodically the ammonia was vented off and fresh ammonia added over a 4½ hour period. The acid value was measured (10.7 mg KOH) and the miniclave cooled to 120° C. Then the miniclave was purged with nitrogen and the sample tipped. The sample was then purified in two different ways. One portion was washed with hexane and dried at room temperature. A second portion was recrystallised from heptane in a refrigerator overnight.

EXAMPLE 3

Slip properties of the isostearamide as prepared according to Example 2 except the product was purified by thin film distillation rather than hexane wash or heptane recrystallisation were measured in Low Density Polyethylene (LDPE) film.

A masterbatch of 2% Isostearamide in Lupolen 2420H LDPE was prepared using a Haake twin screw extruder operating at approximately 180° C. Comparative masterbatches of 2% stearamide (Crodamide™ SRV), 2% erucamide (Crodamide™ ER) and a masterbatch of 2% natural silica were also prepared in the LDPE. Blown films were produced at a gauge of 35 μm containing 500 ppm of slip agent both with and without 500 ppm natural silica as a blocking agent.

Static and kinetic coefficients of friction (CoF) were measured in accordance with ASTM D1894 over a period of several weeks. The results are reported in Table 3 below

TABLE 3

| Time (hours) | No additive Static CoF | No additive Kinetic CoF | Refined isostearamide Static CoF | Refined isostearamide Kinetic CoF | Refined isostearamide with silica Static CoF | Refined isostearamide with silica Kinetic CoF | Stearamide (comparative) Static CoF | Stearamide (comparative) Kinetic CoF | Erucamide (comparative) Static CoF | Erucamide (comparative) Kinetic CoF |
|---|---|---|---|---|---|---|---|---|---|---|
| 0.1 | 1.34 | 1.25 | 0.87 | 0.72 | 0.54 | 0.48 | 1.02 | 0.93 | 0.60 | 0.49 |
| 1 | 1.42 | 1.29 | 0.37 | 0.32 | 0.24 | 0.18 | 0.89 | 0.83 | 0.18 | 0.13 |
| 2 | 1.30 | 1.18 | 0.31 | 0.25 | 0.21 | 0.15 | 0.90 | 0.84 | 0.18 | 0.11 |
| 4 | 1.37 | 1.26 | 0.26 | 0.23 | 0.19 | 0.14 | 0.89 | 0.83 | 0.16 | 0.10 |
| 24 | 1.14 | 1.08 | 0.29 | 0.19 | 0.17 | 0.12 | 0.69 | 0.63 | 0.19 | 0.10 |
| 48 | 1.22 | 1.12 | 0.28 | 0.17 | 0.17 | 0.13 | 0.73 | 0.67 | 0.19 | 0.11 |
| 168 | 1.08 | 0.97 | 0.31 | 0.17 | 0.18 | 0.13 | 0.66 | 0.58 | 0.19 | 0.13 |
| 336 | 1.01 | 0.87 | 0.30 | 0.18 | 0.18 | 0.12 | 0.69 | 0.62 | 0.23 | 0.12 |
| 744 | 0.96 | 0.89 | 0.32 | 0.19 | 0.20 | 0.13 | 0.76 | 0.66 | 0.23 | 0.13 |
| 2232 | 1.16 | 1.07 | 0.34 | 0.22 | 0.26 | 0.18 | 0.71 | 0.61 | 0.25 | 0.14 |

EXAMPLE 4

Slip properties of the isostearamide as prepared according to Example 2 except the purification method was thin film distillation, were measured in polypropylene homopolymer (hPP) and polypropylene copolymer (cPP)

A masterbatch of 2% Isostearamide (as prepared in Example 2) in hPP (Borealis HD204) and separately cPP (RD208) were prepared using a Haake twin screw extruder operating at approximately 180° C. Comparative masterbatches of 2% stearamide (Crodamide™ SRV), 2% erucamide (Crodamide™ ER) and a masterbatch of 2% natural silica were also prepared in the hPP and cPP. Cast films were produced at a gauge of 50 μm containing 1500 ppm of slip agent with 1500 ppm natural silica as a blocking agent.

Static and kinetic coefficients of friction (CoF) were measured using a modified version of ASTM D1894 over a period of several weeks. The results are reported in Tables 4 and 5 below

TABLE 4

| Time (hours) | No additive Static CoF | No additive Kinetic CoF | Refined isostearamide with silica Static CoF | Refined isostearamide with silica Kinetic CoF | Silica (comparative) Static CoF | Silica (comparative) Kinetic CoF | Stearamide with silica (comparative) Static CoF | Stearamide with silica (comparative) Kinetic CoF | Erucamide With silica (comparative) Static CoF | Erucamide with silica (comparative) Kinetic CoF |
|---|---|---|---|---|---|---|---|---|---|---|
| 0.1 | 3.73 | 2.41 | 1.72 | 1.29 | 2.04 | 1.51 | 1.68 | 1.29 | 1.56 | 1.19 |
| 2 | 2.80 | 1.85 | 1.25 | 1.01 | 1.62 | 1.254 | 1.09 | 0.98 | 0.99 | 0.90 |
| 4 | 2.88 | 1.90 | 1.08 | 0.96 | 1.62 | 1.25 | 1.03 | 0.96 | 0.94 | 0.89 |
| 24 | 2.09 | 1.55 | 0.84 | 0.79 | 1.36 | 1.08 | 0.90 | 0.85 | 0.81 | 0.76 |
| 48 | 2.09 | 1.53 | 0.76 | 0.73 | 1.30 | 1.07 | 0.85 | 0.81 | 0.73 | 0.70 |
| 168 | 2.08 | 1.53 | 0.61 | 0.58 | 1.33 | 1.07 | 0.77 | 0.73 | 0.64 | 0.61 |
| 336 | 1.84 | 1.35 | 0.55 | 0.53 | 1.09 | 0.96 | 0.75 | 0.70 | 0.56 | 0.50 |
| 744 | 1.85 | 1.25 | 0.43 | 0.41 | 1.08 | 0.96 | 0.61 | 0.57 | 0.44 | 0.41 |

TABLE 5

| Time (hours) | Refined isostearamide with silica Static CoF | Refined isostearamide with silica Kinetic CoF | Silica (comparative) Static CoF | Silica (comparative) Kinetic CoF | Stearamide with silica (comparative) Static CoF | Stearamide with silica (comparative) Kinetic CoF | Erucamide With silica (comparative) Static CoF | Erucamide with silica (comparative) Kinetic CoF |
|---|---|---|---|---|---|---|---|---|
| 0.1 | | | 2.98 | 2.19 | 2.43 | 1.78 | | |
| 4 | 0.84 | 0.80 | 1.78 | 1.42 | 1.28 | 1.21 | 1.07 | 1.01 |
| 24 | 0.60 | 0.57 | 1.71 | 1.39 | 1.19 | 1.11 | 0.92 | 0.87 |
| 48 | 0.48 | 0.45 | 1.63 | 1.34 | 1.08 | 1.01 | 0.80 | 0.76 |

TABLE 5-continued

| Time (hours) | Refined isostearamide with silica Static CoF | Refined isostearamide with silica Kinetic CoF | Silica (comparative) Static CoF | Silica (comparative) Kinetic CoF | Stearamide with silica (comparative) Static CoF | Stearamide with silica (comparative) Kinetic CoF | Erucamide With silica (comparative) Static CoF | Erucamide with silica (comparative) Kinetic CoF |
|---|---|---|---|---|---|---|---|---|
| 168 | 0.33 | 0.28 | 1.63 | 1.30 | 0.90 | 0.85 | 0.58 | 0.55 |
| 336 | 0.30 | 0.25 | 1.35 | 1.18 | 0.70 | 0.62 | 0.46 | 0.43 |
| 744 | 0.28 | 0.21 | 1.35 | 1.22 | 0.62 | 0.59 | 0.31 | 0.25 |

EXAMPLE 5

Torque application and torque release data were measured for a GD4744 HDPE (available ex LyondellBasell) closure on a PET bottle.

The bottle was placed in a UCP torque tester. For torque application the closure was applied manually to the bottle until it just started to grip. Then a torque of 5 lb in was applied quickly using an RS 575-633 torque wrench. Then a 90° clockwise torque was applied at a constant rate of application and held for 10 seconds. A reading was then taken for the maximum torque applied to the closure.

Torque release was then measured after a period of 7 days by removal of the closure using the torque wrench as if it was being removed by hand. The maximum torque reading on the UCP torque tester was then noted.

The results are reported in Table 6 below. Each result is derived from the mean of ten values.

TABLE 6

| | Average Torque application (lbin) | Standard Deviation | Average Release Torque (lbin) | Standard Deviation |
|---|---|---|---|---|
| No slip additive | 15.9 | 1.20 | 5.8 | 1.64 |
| 2000 ppm refined isostearamide (ex Example 2) | 15.1 | 0.69 | 5.2 | 1.64 |
| 2000 ppm behenamide | 15.8 | 0.75 | 5.4 | 1.36 |

EXAMPLE 6

Oxidative Stability Testing

Measurement of Oxidative Induction Time.

Twelve 5 g samples of the isostearamide as prepared in Example 2 were melted and placed into Petri dishes. Ten of the samples were placed in a thermostatically controlled fan oven set at 120° C. The other two samples were left at room temperature as control. Two samples were removed from the oven after 20, 30, 40, 50 and 60 hours respectively. Each sample was dissolved in 95 ml of ethanol and the absorbance at 420 nm measured on a UV/VIS spectrophotometer (A1). The absorbance of ethanol itself was then recorded at 420 nm (A2). The absorbance of each sample was calculated as A1-A2. The mean absorbance for each pair of samples was plotted against time and the oxidative induction time determined at the point at which the absorbance at 420 nm was seen to increase significantly.

The experiment was then repeated with 12 samples of two commercial oleamide products, Crodamide ER and Crodamide VRX.

The results are shown in Table 7

TABLE 7

| | Absorption at 420 nm | | |
|---|---|---|---|
| Time (hrs) | Isostearamide | Crodamide ER | Crodamide VRX |
| 0 | 0.004 | 0.007 | 0.002 |
| 16 | 0.009 | 0.035 | 0.004 |
| 24 | 0.018 | 0.222 | 0.014 |
| 48 | 0.016 | 0.697 | 0.098 |
| 72 | 0.018 | 1.343 | 1.165 |
| 96 | 0.027 | 1.428 | 1.487 |

The data clearly indicates that the product of the invention is much more oxidatively stable than unsaturated amides that are currently used commercially.

EXAMPLE 7

Preparation of isostearic acid, wherein at least 60% by weight of the acid molecules have monoalkyl branches and less than 25% by weight of the acid molecules have polyalkyl branches by a single stage clathration process.

Commercial Isostearic acid (300 g) and Urea prills (500 g) were refluxed in industrial methylated spirits (770 g, 95/5 by wt mixture with water) for 1 hour. The solution was allowed to cool to 20° C. The crystals that formed were filtered off and placed in a conical flask with 2% brine solution. The aqueous layer was drained off and the process was repeated with the addition of further brine solution and draining off of the aqueous layer. The resultant refined fatty acid was found to have 69.3% by weight of the acid molecules having monoalkyl branching.

EXAMPLE 8

The refined fatty acid of Example 7 was converted to the corresponding refined fatty acid amide using the method as described in Example 2.

EXAMPLE 9

Kinetic coefficients of friction were measured over a range of 3000 hrs for a range of amides with differing levels of % monomethyl branching for 750 ppm of amide in LDPE. The results are shown in Table 8 and clearly show that the kinetic coefficient of friction is significantly reduced as the level of % monomethyl branching increases.

TABLE 8

| % monomethyl branching in refined amide | Time in Hours | | | | | | | | |
|---|---|---|---|---|---|---|---|---|---|
| | 0.1 | 1 | 2 | 4 | 24 | 48 | 168 | 336 | 2190 |
| | Kinetic Coefficient of friction | | | | | | | | |
| No amide | 1.096 | 1.131 | 1.109 | 1.089 | 1.024 | 1.050 | 0.942 | 1.039 | 0.897 |
| 42.7 (comparative) | 0.959 | 0.530 | 0.424 | 0.361 | 0.349 | 0.361 | 0.365 | 0.309 | 0.332 |
| 62.3 | 0.741 | 0.366 | 0.315 | 0.282 | 0.270 | 0.260 | 0.236 | 0.249 | 0.246 |
| 72.0 | 0.633 | 0.344 | 0.249 | 0.203 | 0.200 | 0.174 | 0.196 | 0.156 | 0.179 |
| 80.6 | 0.599 | 0.310 | 0.246 | 0.205 | 0.218 | 0.204 | 0.151 | 0.163 | 0.160 |

EXAMPLE 10

The colour stability of a range of amides with differing levels of % monomethyl branching was measured as follows. A sample of each amide was placed in a LICO tube and placed in an oven at 120° C. The tubes were taken out of the oven at varying times up to 80 hours and their colours measured using a LICO colorimeter. The results are shown in Table 9.

TABLE 9

| % monomethyl branching in refined amide | Time in Hours | | | | | | | |
|---|---|---|---|---|---|---|---|---|
| | 0 | 7 | 24 | 31 | 48 | 55 | 72 | 79 |
| | Colour Change in G | | | | | | | |
| 42.7 (comp.) | 0 | 0.9 | 2.0 | 2.4 | 3.1 | 3.3 | 3.8 | 3.9 |
| 62.3 | 0 | 0.3 | 1.1 | 1.6 | 2.7 | 2.9 | 3.7 | 4.0 |
| 72.0 | 0 | 0.2 | 0.8 | 1.2 | 1.9 | 2.1 | 2.8 | 3.1 |
| 80.6 | 0 | 0.1 | 0.5 | 0.7 | 1.5 | 1.7 | 2.5 | 2.9 |
| Erucamide (comp) | 0 | 0.8 | 2.5 | 2.4 | 3.5 | 3.9 | 4.8 | 5.2 |
| Behenamide (comp) | 0 | 1.1 | 2.2 | 3.6 | 3.6 | 3.7 | 4.3 | 4.6 |

It is clear from the data in Table 9 that the refined amides of the current invention have enhanced stability as compared to the comparative products.

EXAMPLE 11

The iodine value, g Iodine per 100 g, was measured for a range of refined fatty acids. The results are shown in Table 10.

TABLE 10

| % monomethyl branching in refined fatty acid | How refined fatty acid prepared | Iodine Value (g $I_2$ per 100 g) |
|---|---|---|
| 62.3 | Two stage clathration as in with 8000 g commercial isostearic acid, 8000 g methanol and 1600 g urea prills | 1.53 |
| 72.0 | Two stage clathration as in with 8000 g commercial isostearic acid, 8000 g methanol and 1600 g urea prills | 0.67 |
| 80.6 | Two stage clathration with 752 g commercial isostearic acid, 750 ml methanol and 150.1 g urea | 0.90 |
| >85 | Two stage clathration with 500 g commercial isostearic acid, 500 g urea and 2500 ml of methanol | 0.35 |

All of the refined acids and hence all of refined amides of this invention derived from these refined acids have iodine values much lower than those in the JP prior art, JP48-13935, of between 3 and 10.

The invention claimed is:

1. A mixture of branched, primary fatty acid amides of formula I:

$$R\text{—}CO\text{—}NH_2$$

wherein:
  i) R is a saturated, branched hydrocarbon chain having 11 to 23 carbon atoms;
  ii) at least 60% by weight of the R—CO—$NH_2$ molecules are monoalkyl branched, said monoalkyl branches comprising methyl branches and ethyl branches; and
  iii) less than 25% by weight of the R—CO—$NH_2$ molecules are polyalkyl branched.

2. The branched primary fatty acid amides of claim 1, wherein at least 70% by weight of the R—CO—$NH_2$ molecules have monoalkyl branches.

3. The branched primary fatty acid amides of claim 1, wherein less than 20% by weight of the R—CO—$NH_2$ molecules have polyalkyl branches.

4. The branched primary fatty acid amides of claim 1, wherein R has 13 to 23 carbon atoms.

5. The branched primary fatty acid amides of claim 1, wherein the monoalkyl branches further comprise propyl branches.

6. The branched primary fatty acid amides of claim 1, wherein the monoalkyl branches are at least 80% methyl branches.

7. The branched primary fatty acid amides of claim 1, wherein the monoalkyl branches are positioned in the middle of the hydrocarbon chain R.

8. The branched primary fatty acid amides of claim 1, which has an iodine value of not more than 2.8 g iodine per 100 g.

9. A process for preparation of a mixture of branched primary fatty acid amides of formula I:

$$R\text{—}CO\text{—}NH_2$$

comprising:
  a) refining a mixture of saturated branched fatty acids of formula $R^2COOH$ to form a mixture of RCOOH, wherein $R^2$ has 11 to 23 carbon atoms;

b) amidating the mixture of RCOOH with ammonia in the presence of a catalyst; and
c) purifying the resultant mixture of branched primary fatty acid amides of formula I;
wherein:
  i) R is a saturated, branched hydrocarbon chain having 11 to 23 carbon atoms;
  ii) at least 60% by weight of the R—CO—NH$_2$ molecules are monoalkyl branched, said monoalkyl branches comprising methyl branches and ethyl branches; and
  iii) less than 25% by weight of the R—CO—NH$_2$ molecules are polyalkyl branched.

10. A process for preparation of a branched primary fatty acid amide of formula I:

R—CO—NH$_2$ comprising:
  a) refining a saturated branched fatty acid of formula R$^2$COOH to form RCOOH, wherein R$^2$ has 11 to 23 carbon atoms, and wherein the refining method is clathration with urea and a lower alcohol; followed by
  b) amidating the RCOOH with ammonia in the presence of a catalyst; then
  c) purifying the resultant branched primary fatty acid amide of formula I;
wherein:
  i) R is a saturated, branched hydrocarbon chain having 11 to 23 carbon atoms;
  ii) at least 60% by weight of the R—CO—NH$_2$ molecules are monoalkyl branched; and
  iii) less than 25% by weight of the R—CO—NH$_2$ molecules are polyalkyl branched.

11. A method of improving slip and/or anti-blocking properties of a polymer, comprising: adding to the polymer a branched, primary fatty acid amide of formula I:

R—CO—NH$_2$ where R is a saturated, branched hydrocarbon chain having 11 to 23 carbon atoms wherein at least 60% by weight of the R—CO—NH$_2$ molecules have monoalkyl branches and less than 25% by weight of the R—CO—NH$_2$ molecules have polyalkyl branches.

12. A method of improving mould release property of a polymer, comprising: adding to the polymer a branched, primary fatty acid amide of formula I:

R—CO—NH$_2$ where R is a saturated, branched hydrocarbon chain having 11 to 23 carbon atoms wherein at least 60% by weight of the R—CO—NH$_2$ molecules have monoalkyl branches and less than 25% by weight of the R—CO—NH$_2$ molecules have polyalkyl branches.

13. A process for increasing slip and reducing block of polyolefin films, both monolayer and coextruded, which process comprises fabricating said films and sheets from a polymer composition including a branched, primary fatty acid amide of formula I:

R—CO—NH$_2$ where R is a saturated, branched hydrocarbon chain having 11 to 23 carbon atoms wherein at least 60% by weight of the R—CO—NH$_2$ molecules have monoalkyl branches and less than 25% by weight of the R—CO—NH$_2$ molecules have polyalkyl branches.

14. A polymer composition comprising
  (a) 50 to 99.98% by weight of a polyolefin polymer
  (b) 0.02 to 3% by weight of a branched, primary fatty acid amide of formula I:

R—CO—NH$_2$ where R is a saturated, branched hydrocarbon chain having 11 to 23 carbon atoms wherein at least 60% by weight of the R—CO—NH$_2$ molecules have monoalkyl branches and less than 25% by weight of the R—CO—NH$_2$ molecules have polyalkyl branches.

15. A polymer composition comprising
  (a) 50 to 99.9% by weight of a polystyrene polymer
  (b) 0.1 to 3% by weight of a branched, primary fatty acid amide of formula I:

R—CO—NH$_2$ where R is a saturated, branched hydrocarbon chain having 11 to 23 carbon atoms wherein at least 60% by weight of the R—CO—NH$_2$ molecules have monoalkyl branches and less than 25% by weight of the R—CO—NH$_2$ molecules have polyalkyl branches.

16. The process of claim 9, wherein the refining method is clathration with urea and a lower alcohol.

17. A method of improving slip and/or anti-blocking properties of a polymer, comprising: adding to the polymer the mixture of branched, primary fatty acid amides of claim 1.

18. A method of improving mould release property of a polymer, comprising: adding to the polymer the mixture of branched, primary fatty acid amides of claim 1.

19. A process for increasing slip and reducing block of polyolefin films, both monolayer and coextruded, comprising fabricating said films and sheets from a polymer composition including the mixture of branched, primary fatty acid amides of claim 1.

20. A polymer composition, comprising:
  a) 50 to 99.98% by weight of a polyolefin polymer; and
  b) 0.02 to 3% by weight of the mixture of branched, primary fatty acid amides of claim 1.

21. A polymer composition, comprising:
  a) 50 to 99.9% by weight of a polystyrene polymer; and
  b) 0.1 to 3% by weight of the mixture of branched, primary fatty acid amides of claim 1.

* * * * *